United States Patent
Gescheit (10) Patent No.: US 10,874,833 B2
(45) Date of Patent: Dec. 29, 2020

(54) CRADLE INCLUDING OPTICAL INDICATION DEVICE

(71) Applicant: Roche Diagnostics Operations, Inc., Indianapolis, IN (US)

(72) Inventor: Illai J Gescheit, Tel Aviv (IL)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 423 days.

(21) Appl. No.: 14/518,381

(22) Filed: Oct. 20, 2014

(65) Prior Publication Data
US 2015/0151082 A1   Jun. 4, 2015

(30) Foreign Application Priority Data
Oct. 23, 2013   (EP) .................................... 13189895

(51) Int. Cl.
*A61B 5/00*   (2006.01)
*A61M 25/02*   (2006.01)
(Continued)

(52) U.S. Cl.
CPC ......... *A61M 25/02* (2013.01); *A61B 5/14532* (2013.01); *A61B 5/4839* (2013.01); *A61B 5/6802* (2013.01); *A61B 5/742* (2013.01); *A61M 5/1413* (2013.01); *A61M 5/14248* (2013.01); *A61M 5/1723* (2013.01); *A61M 5/5086* (2013.01); *A61B 5/6823* (2013.01);
(Continued)

(58) Field of Classification Search
CPC .. A61M 25/02; A61M 5/5086; A61M 5/1723; A61M 5/1413; A61M 5/14248; A61B 5/6802; A61B 5/4839; A61B 5/742; A61B 5/14532
See application file for complete search history.

(56) References Cited

U.S. PATENT DOCUMENTS

| | | | |
|---|---|---|---|
| 5,138,351 A | * | 8/1992 | Wiegand .................. G03B 7/26 320/111 |
| 6,016,038 A | | 1/2000 | Mueller et al. |

(Continued)

FOREIGN PATENT DOCUMENTS

| | | |
|---|---|---|
| WO | 2000025844 A1 | 5/2000 |
| WO | 200172358 A1 | 10/2001 |

(Continued)

OTHER PUBLICATIONS

Kitronik Ltd; "How colour changing LEDs work"; accessed Dec. 12, 2019; https://www.kitronik.co.uk/blog/how-colour-changing-leds-work/.

*Primary Examiner* — Navin Natnithithadha
*Assistant Examiner* — Andrey Shostak
(74) *Attorney, Agent, or Firm* — Dinsmore & Shohl, LLP (57) ABSTRACT

A cradle and methods of using embodiments of the cradle are described. The cradle has a proximal side and a distal side, where the proximal side has a skin attachment member for releasable attachment to a patient's skin. The distal side includes a device attachment member configured to attach an initially separate medical device. The cradle comprises an electronically controlled optical indication device, the electronically controlled optical indication device being configured to provide optical indications to the patient when the cradle is attached to the patient's skin.

15 Claims, 4 Drawing Sheets (51) Int. Cl.
  *A61B 5/145*   (2006.01)
  *A61M 5/142*   (2006.01)
  *A61M 5/14*    (2006.01)
  *A61M 5/172*   (2006.01)
  *A61M 5/50*    (2006.01)
  *A61B 90/00*   (2016.01)

(52) U.S. Cl.
  CPC ... *A61B 2090/0807* (2016.02); *A61B 2560/04* (2013.01); *A61M 2005/14268* (2013.01); *A61M 2005/1726* (2013.01); *A61M 2205/0227* (2013.01); *A61M 2205/0238* (2013.01); *A61M 2205/3303* (2013.01); *A61M 2205/3306* (2013.01); *A61M 2205/3523* (2013.01); *A61M 2205/3561* (2013.01); *A61M 2205/3569* (2013.01); *A61M 2205/3592* (2013.01); *A61M 2205/50* (2013.01); *A61M 2205/502* (2013.01); *A61M 2205/52* (2013.01); *A61M 2205/583* (2013.01); *A61M 2205/584* (2013.01); *A61M 2205/6063* (2013.01); *A61M 2205/6081* (2013.01); *A61M 2209/01* (2013.01); *A61M 2230/201* (2013.01)

(56) References Cited

U.S. PATENT DOCUMENTS

| | | | |
|---|---|---|---|
| 2007/0100222 A1* | 5/2007 | Mastrototaro | A61B 5/01 600/365 |
| 2007/0106218 A1 | 5/2007 | Yodfat et al. | |
| 2007/0191702 A1* | 8/2007 | Yodfat | A61B 5/14525 600/365 |
| 2009/0292185 A1 | 11/2009 | Funderburk et al. | |
| 2010/0137790 A1* | 6/2010 | Yodfat | A61M 5/14248 604/67 |
| 2010/0317951 A1 | 12/2010 | Rutkowski et al. | |
| 2010/0331652 A1* | 12/2010 | Groll | A61B 5/14532 600/365 |
| 2011/0201911 A1 | 8/2011 | Johnson et al. | |
| 2012/0004602 A1 | 1/2012 | Hanson et al. | |
| 2012/0232520 A1* | 9/2012 | Sloan | A61B 5/14532 604/504 |
| 2013/0100120 A1* | 4/2013 | Sumi | G02B 27/2214 345/419 |
| 2013/0217979 A1 | 8/2013 | Blackadar et al. | |

FOREIGN PATENT DOCUMENTS

| | | | |
|---|---|---|---|
| WO | 2006083831 A1 | 8/2006 | |
| WO | 2007146864 A2 | 12/2007 | |
| WO | 2008110263 A1 | 9/2008 | |
| WO | 2009002455 A1 | 12/2008 | |
| WO | 2009077143 A1 | 6/2009 | |
| WO | 2010028719 A1 | 3/2010 | |
| WO | 2010055504 A1 | 5/2010 | |
| WO | WO 2011064780 A2 * | 6/2011 | A61B 5/1451 |

* cited by examiner

CRADLE INCLUDING OPTICAL INDICATION DEVICE

CROSS REFERENCE TO RELATED APPLICATIONS

The present application claims priority to European Patent Application No. 13189895.9, Oct. 23, 2013, which is hereby incorporated by reference in its entirety.

TECHNICAL FIELD

The present disclosure is directed towards the field of cradles for body-attachable medical devices, ambulatory medical systems including a cradle, and methods for providing optical indications to a patient carrying an ambulatory medical system.

BACKGROUND

Continuous Subcutaneous Insulin Infusion (CSII) is an established and therapeutical advantageous way of treating diabetes mellitus. Under CSII, a diabetic carries a miniaturized infusion device in form of an insulin pump substantially continuously, night and day. The insulin pump infuses minimal quantities of insulin in a substantially continuous way according to a person-specific, generally time-variable infusion schedule or regime, thus providing a so-called basal amount of insulin that is required by the diabetic's body for maintaining a normal or close-to-normal metabolism and in particular blood glucose concentration. Typically, the basal administration schedule follows a generally circadian cycle and is pre-set by a healthcare professional. In addition, insulin pumps are designed to administer larger insulin quantities, so called boli, within a short period of time on demand.

For a number of years, insulin pumps have virtually always been designed as battery-powered and self-contained devices with a footprint comparable, in recent years, to a credit card. This footprint allows them to be carried in a trousers' pocket, with a corresponding holster and a belt, as necklace, or the like. Via infusion tubing of typically 0.5 to 1.5 m length, such devices are coupled to a subcutaneous infusion cannula. A typically syringe-like drug container that is received by a container compartment of the device as well as infusion tubing and the infusion cannula are designed as disposables and are replaced by the patient after a relatively short lifetime of typically a number of days. Over the last years, comparatively sophisticated devices have become available that may include wireless coupling to a remote controller, to a standard computer like a PC, or to glucose measurement devices or continuous glucose monitors (CGMs). A typical, commercially available state-of-the-art system includes the ACCU-CHEK® Combo Spirit infusion device and the ACCU-CHEK® Combo Aviva remote controller and glucose measurement device, provided by Roche Diagnostics, Inc.

SUMMARY

According to at least one embodiment of the present disclosure, a cradle is disclosed. The cradle has a proximal side, where the proximal side has a skin attachment member for releasable attachment to a patient's skin. The cradle may further have a distal side, the distal side having an infusion device attachment member for attaching an initially separate medical device.

The cradle according to at least one embodiment is a structurally distinct adapter element that is designed for attachment between the patient's skin and the medical device in a sandwich-like way. The medical device is accordingly attachable to the skin via the cradle. The footprint of a typical cradle largely corresponds to the footprint of the proximal, skin-facing side of the medical device, which, however, is not essential. The cradle may be essentially flat and disk-like shape.

The cradle may further include an electronically controlled optical indication device, the optical indication device being arranged to provide optical indications to the patient when the cradle is attached to the patient's skin.

In some embodiments, the optical indication device includes at least one of an electrochromatic device, an organic or non-organic light emitting diode, or a liquid crystal element.

The cradle may either include a single indicator, such as a single light emitting diode (LED), or a number of distinct indicators, such as a number of, e.g. three LEDs, or a combination of one or more LEDs and an electrochromatic device, in at least one embodiment.

A liquid crystal element may be realized as liquid crystal display (LCD) as known in the art. Alternatively, it may be realized by an electronic skin, the electronic skin including a liquid crystal material and covering, fully, or partly, a cradle body of the cradle that may be formed from any suited state-of the art material, such as plastics. Designing such an electronic skin may be carried out in an analogue way to the disclosure of US 2010/0317951 A1.

In some embodiments including an electrochromatic device, the cradle is formed, at least in part, from electrochromatic material and/or is coated, at least at part, with an electrochromatic coating. The cradle may either be formed, fully or partly, from electrochromatic material, or may be formed from any suited state-of the art material, such as plastics, and subsequently be fully or partly coated by an electrochromatic coating.

Electrochromatic materials reversibly change colour and/or transmission/reflexion properties when a burst of electrical charge is applied. Typical electrochromatic materials include polyaniline, viologens, polyoxotungstates, and tungsten oxide.

In some embodiments, the cradle includes a communication interface in operative coupling to the optical indication device, the communication interface being further designed to operatively couple to the medical device.

The communication interface may be designed by electrical cradle contacts that are arranged on the cradle such that they contact, in an operative state, corresponding medical device contacts, thus establishing a galvanic coupling.

Alternatively, the communication interface may be designed for non-galvanic coupling and be designed, e.g., as electro-optical interface, capacitive interface or short range radio frequency (RF) interface.

In some embodiments, the cradle includes an electronic indication device control unit in operative coupling to the optical indication device.

The indication device control unit may include all circuitry that is required for actuating and driving the optical indication device and is typically realized based on solid-state semiconductor technology. The indication device control unit may especially include components such as one or more microcontrollers, ASICS, logic circuitry, transistors, and the like.

In some embodiments, the optical indication device is designed to provide indications in at least two different colours.

To provide indications in at least two different colours, the optical indication device may, e.g., include a number of separate LEDs of different colour that may favourably be independently controlled. Similarly, one or more multi-colour-LEDs may be used. In further variants, the optical indication device may include a multi-colour liquid crystal element or a colour-changing electrochromatic element.

In some embodiments, the optical indication device is designed to change colour and/or transparency in a continuous or quasi-continuous way.

A continuous or quasi-continuous colour or transparency change is particularly favourable for indicating, via the colour, continuous data such as the glucose value or the remaining drug volume in a container, as will be further described below.

In some embodiments, the cradle includes a skin-piercing device or a skin-piercing device attachment member for attaching an initially separate skin-piercing device.

In some embodiments including a skin-piercing device, the skin-piercing device includes a continuous glucose sensor and the cradle couples or is configured to couple in an operative state the continuous glucose sensor to the optical indication device such that the optical indication device provides a glucose indication of the patient.

The continuous glucose sensor of such an embodiment may be designed in a variety of ways. It may especially be an electro-chemical cannula sensor as generally known in the art. In addition to the continuous glucose sensor, the cradle of such an embodiment may include further associated circuitry such as analogue and/or digital filters, amplifiers, signal conditioning circuitry, sensor power supply circuitry or the like. Alternatively, those components may, completely or partly, be included in the medical device.

In some embodiments involving a glucose sensor, the cradle is designed to provide the glucose indication independent of a presence of the medical device. As explained before, a patient may whish or need to occasionally remove a medical device that is normally attached to the skin while keeping the cradle attached to the skin. In such a situation, checking of the glucose value is still desirable, e.g. during sportive activities. For this type of embodiment, all required circuitry, including power supply, that is required for operative coupling the glucose sensor and the optical indication device, are part of the continuous glucose sensor and/or the cradle, thus forming a complete CGM.

In a variant of such an embodiment, glucose-related data may additionally be transmitted, in an operative state, to a medical device, e.g. for record keeping purposes. In embodiments where the medical device is or includes a drug infusion device, the glucose related data may further be used for temporarily suspending or reducing insulin delivery in case of low glucose values as disclosed, e.g., in the WO 2009/002455 A1 or the WO 2006/083831 A1. Blood-glucose related data, may, by the cradle itself or the medical device attached to the cradle, also be transmitted to further remote devices, such as a remote controller, a smart phone, or the like, for analysis and record keeping purposes, and the like.

In some embodiments, the skin-piercing device includes an infusion cannula. An infusion cannula or an infusion cannula attachment member may be provided additionally or alternatively to a glucose sensor or glucose sensor attachment member. If both a glucose sensor and an infusion cannula are foreseen, they may be provided integral with each other, i.e., with a common skin-piercing device, or they may be separate but in proximity, e.g. with a distance up to 1.5 cm relative to each other, or they may have a larger relative distance. In embodiments where attachment members are provided, a glucose sensor attachment member and an infusion cannula attachment member may be provided separately on the cradle or in form of a combined attachment member.

According to a further aspect, the present disclosure is directed towards an ambulatory medical system. The medical system may include a cradle as discussed above and further below in the context of exemplary embodiments. The medical system may further include a medical device that is initially separate and is designed for attachment to the cradle via the medical device attachment member.

The ambulatory medical system may be configured such that, in an operative state, the medical device and the optical indication device operatively couple such that the optical indication device provides indication to the patient with respect to at least one of an operative state or operative parameter of the medical device or the occurrence of a medical device hazard.

For the medical device including a drug infusion device, an operative state that may be indicated may include, e.g., whether the system is currently active or drug delivery is temporarily suspended or basal delivery is reduced below a scheduled value because of sportive activities or the like. Operative parameters that may be indicated may, e.g., be a remaining drug volume in the cartridge, the charging state of a power supply such as battery, or a remaining lifetime of the drug infusion device as a whole or any of its components, especially the infusion cannula. For many of those operative parameters, it is helpful in many situations for the diabetic to get a rough and semi-quantitative estimate, while a precise numeric value may not be required in many situations.

In embodiments where a number of distinct optical indicators are present or an indicator is designed to provide indications in a number of distinct colours, semi-quantitative indication may be provided, e.g. in a traffic-light like way. e.g., a green indication may be provided if the reservoir is at least filled to $\frac{1}{32}$ of its full volume, yellow if it filled to a volume of about $\frac{1}{2}$ to about $\frac{1}{4}$, and red if it filled to a volume below $\frac{1}{4}$. In embodiments where the indication device allows a continuous or quasi-continuous colour- or transparency indication, the same principle may be applied on a continuous or quasi-continuous basis.

Medical device hazards are situations in which correct operation of the medical device is not given and immediate user action is required. For a drug infusion device, medical device hazards are, e.g. an empty drug reservoir, an empty power supply battery, a blocked or leaking infusion line, or a device error. In addition or alternatively to medical device hazards, the optical indication device may alert the user of any further situation where some user action or system checking by the user should be carried out, such as testing the tightness of an infusion cannula connection.

In some embodiments, the medical device includes a drug infusion device, the drug infusion device including an infusion cannula or an outlet that is designed to fluidically couple to an infusion cannula comprised by the cradle or attached to the cradle via a cannula attachment member.

In the context of CSII therapy, the drug infusion device may be designed to deliver insulin to the patient in accordance with a time-variable basal administration regime and to further deliver drug boli on demand.

Designs of the drug infusion device that may be used in the context of the present disclosure are disclosed, e.g., in the WO 2010/10055504 A1, WO 2001/72358 A1, WO 2009/077143 A1, or WO 20000/25844 A1. Alternatively, the drug infusion device may be based on a dosing unit as disclosed in the WO 20008/110263 A1 and the WO2010/028719 A1. The drug infusion device may alternatively be designed according to further principles that are known in the art for this type of application, and use, e. g. a micromembrane pump or micro peristaltic pump.

In some embodiments, the medical device includes continuous glucose monitor CGM circuitry. The CGM generally includes functional units and circuitry as required to provide an operable CGM system. The glucose sensor itself may, in dependence of the specific embodiment, be part of the medical device or separate from the medical device and be a structural part of or attached to the cradle.

In some embodiments where the medical device includes a drug infusion device, continuous glucose monitoring circuitry may be present in the drug infusion device, e.g. in form of a glucose data processing unit. The glucose data processing unit may receive glucose related data, such as a signal provided by the continuous glucose sensor, and include capabilities such as comparison with a low and/or high glucose thresholds, trend analysis, glucose prediction, and the like. Such an embodiment may allow the cradle with the continuous glucose sensor to operate in a stand-alone way when the drug infusion device is temporarily not attached. In this situation, a pure indication of the current glucose value may be provided that require only a minimum amount of circuitry and power consumption. More advanced capabilities, however, may be present when the drug infusion device is in place, i.e. attached to the cradle and the glucose data processing unit is accordingly present.

According to another aspect of the present disclosure, a method for providing optical indications to a patient carrying an ambulatory medical system is disclosed. The method may include providing a cradle, the cradle having a proximal side, the proximal side having a skin attachment member for releasably attachment to a patient's skin. The cradle may further have a distal side, the distal side having a medical device attachment member for attaching an initially separated medical device.

The cradle may further include an electronically controlled optical indication device, the optical indication device being arranged to provide optical indications to the patient when the cradle is attached to the patient's skin. The method may further include controlling the optical indication device to provide the optical indications.

In some embodiments, the method may include providing a continuous glucose sensor and controlling the optical indication device to provide a glucose indication of the patient.

In some of the embodiments of the present disclosure, controlling the optical indication device may include controlling the optical indication device to change its colour in dependence of a glucose value of the patient.

In some embodiments, the method may include providing a medical device including a drug infusion device, the drug infusion device being designed for subcutaneous drug delivery and being initially separate and being designed for attachment to the cradle via the infusion device attachment member. The method may further include controlling the optical indication device to provide indication to the patient with respect to at least one of an operative state of the drug infusion device or the occurrence of a drug infusion hazard.

A cradle in accordance with the present disclosure may be used as part of an ambulatory medical system in accordance with the present disclosure. Similarly, a cradle and/or an ambulatory medical system may be used to carry out an indication method in accordance with the present disclosure. Therefore, disclosed embodiments of cradles and ambulatory medical systems disclose, at the same time, a corresponding indication method and vice versa.

BRIEF DESCRIPTION OF THE DRAWINGS

The drawings are not intended to be limiting in any way, and it is contemplated that various embodiments of the present disclosure may be carried out in a variety of other ways, including those not necessarily depicted in the drawings. The accompanying drawings incorporated in and forming a part of the specification illustrate several aspects of embodiments of the present disclosure, and together with the description serve to explain the principles of the present disclosure; it being understood, however, that this invention is not limited to the precise arrangements shown.

DETAILED DESCRIPTION

In the present disclosure, a device that is designed to be attached to a patient's skin via a cradle and fulfils—alone or in combination with further elements or devices—a diagnostic and/or therapeutic function, is referred to as "medical device". Two examples of medical devices that are especially referred to are insulin pumps and continuous glucose monitors (CGMs) as described before. For a CGM, the glucose sensor may be part of or separate from the CGM as such.

In the present disclosure, the cradle by which the medical device is attached to the skin is further distinct from and not part of the medical device as such. In some embodiments however, a CGM may, fully or partly, be part of the cradle and distinct from a separate medical device, such as an insulin pump, attached to the cradle.

The cradle, in at least one embodiment, may—in dependence of the diabetic's individual needs and the type of medical device—further have a longer lifetime than the medical device, such that the same cradle may be used in combination with two or more medical devices in sequence. Providing an optical indication device as part of the cradle may allow its re-use.

The present disclosure aims at providing improvements to ambulatory infusion systems that include a cradle.

In all figures, reference to positions of certain elements or to directions, such as "top", "bottom", upper", "lower", "left", right", refer, if not stated differently, to positions and directions in the figures and are meant to improve their understanding. They are generally not identical to positions and directions of the elements during application. Where reference is made to elements when attached to a patient's skin, an upright standing body position is generally assumed.

Figure 1A:
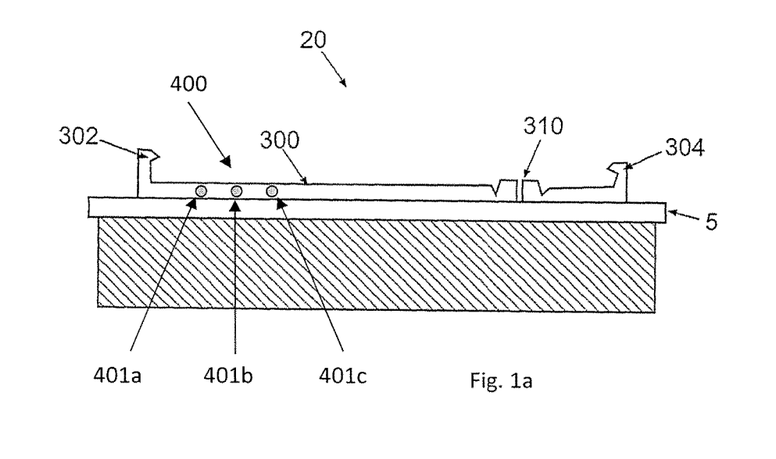
FIGS. 1a and 1b show an exemplary cradle in accordance with the present embodiment in a side view and a top view, respectively in a schematic way.
Figure 1B:
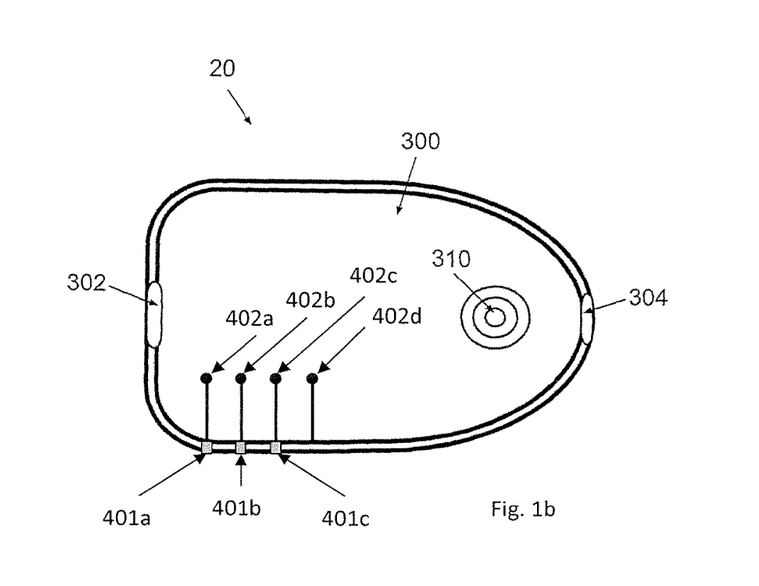

FIG. 1a and FIG. 1b schematically show a cradle 20 in accordance with the present disclosure in side view and top view, respectively. In at least one embodiment, the cradle used in combination with a drug infusion device as a medical device, in particular a drug infusion device for CSII therapy. Alternatively, however, the cradle may be used in combination with other medical devices, in particular a CGM. Functionality of a drug infusion device and a continuous glucose monitor may further be integrated into a common medical device.

Cradle 20 includes cradle base 300 that may be made from injection-moulded plastics. At its proximal side, cradle base 300 has an adhesive layer (not referenced) that serves as an attachment member for attaching the cradle to a diabetic's skin 5. At its distal side, cradle base 300 has a well 310. Well 310 constitutes a passageway through which an infusion cannula can be inserted into the patient's skin. Locking arrangements (not shown), such as latches, may be provided for securing the infusion cannula to well 310. Well 310 accordingly serves as a cannula attachment member. Cradle base 300 may also include infusion device anchoring latches 302, 304 that serve as an infusion device attachment member. Anchoring latches 302, 304 may be designed for a releasable and reconnectable attachment of the drug infusion device.

Cradle 20 further includes optical indication device 400 that is exemplary realized by a set of three distinct LEDs 401a, 401b, 401c which may be different colours. LEDs 401a, 401b, 401c are arranged on cradle base 300 in a way that allows direct visual access when cradle 20 is attached to the diabetic's abdomen region with LEDs 401a, 401b, 401c pointing upwards with respect to the diabetics body, i.e. towards his or her head.

A communication interface is provided in the form of electrical contact elements 402a, 402b 402c, 402d, with one electric contact element being distinct for each of LEDs 401a, 401b, 40c, and one being common. Corresponding counter electrodes, such as spring-loaded contact pins, are provided on a proximal side of the drug infusion device that faces the skin. LEDs 401a, 401b, 401c and contact elements are wired via conductive paths (not shown) that may be screen-printed, or realized in Moulded Interconnected Device (MID) technology, as wires buried in the plastic body of cradle base 300, or the like.

In a variant, a second redundant optical indication device of generally identical design is assembled on the opposite top side of cradle base 300, such that convenient optical indications are possible for a larger range of orientations of cradle 20 relative to the patient's body. In a further variant, cradle 20 is designed symmetrically in left-right direction, including two symmetrically arranged wells, thus allowing a drug infusion device to be attached in different ways— resulting in the cannula position also being different, with LEDs 401a, 401b, 401c always pointing towards the diabetic's head. In such embodiments including more than one redundant optical indication devices, all of them may be activated in parallel for providing optical indications. Alternatively, the medical device may selectively only activate the indication device that is best visible for the patient, i.e. pointing towards his or her head.

In a further variant, optical indication device 400 may, additionally or alternatively to LEDs 401a, 401b, 401c, include electrochromatic elements, e.g. by forming cradle base 300 fully or partly from electrochromatic material. Forming a number of sections or even the whole cradle base 300 from electrochromatic material is an efficient way for enabling optical indication substantially independent of the device orientation relative to the patient's body. One or more liquid crystal elements may be provided in a similar way.

FIG. 2a to FIG. 2h illustrate how a medical device, generally referred to as ref. 10, and cradle 20 may be combined and cooperate as ambulatory medical system. For the sake of clarity and conciseness, only those functional and structural units as well as operative connections between those units are shown and discussed in the following that are of relevance in context of the present disclosure.

Figure 2A:
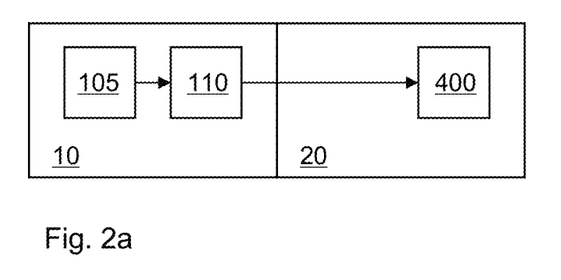
FIGS. 2a, 2b, 2c, 2d, 2e, 2f, 2g, and 2h schematically show medical systems with a cradle and a medical device.

In the example of FIG. 2a, medical device 10 includes medical device control circuitry 105 and indication device control unit 110. Via a communication interface (not referenced), indication device control unit 110 couples to and thereby controls operation of optical indication device 400. Since all control circuitry for optical indication device 400 is, for this embodiment, included in medical device 10, optical indication device 400 is operable only with medical device 10 being attached and thereby operatively coupled to cradle 20. Indication device 400 of this embodiment is used to provide indication to the patient with respect to at least one of an operative state or operative parameter of the medical device or the occurrence of a medical device hazard. Medical device 10 of this embodiment may, e.g., be a drug infusion device. This type of embodiment may be advantageous if medical device 10 is comparatively high-priced and/or has a comparatively long useful life time, while disposable cradle 20 should be as simple in design and as cheap in production as possible.

Figure 2B:
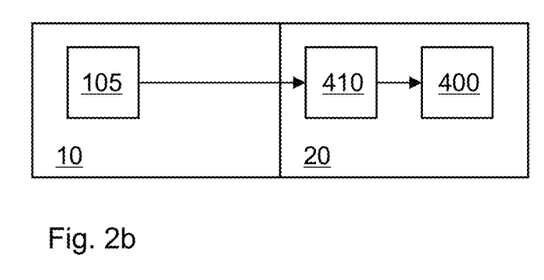

In the example of FIG. 2b, the overall design is similar to the one of FIG. 2a. Indication device control unit 110, however, is not part of medical device 10. Instead, indication device control unit 410 is provided as part of cradle 20 and is in operative coupling with medical device 10 via a communication interface (not referenced). For this type of embodiment, the control circuitry that is required for controlling optical indication device 400 is accordingly part of cradle 20, while information that shall be indicated is received from medical device 10, requiring presence of medical device 10 for providing indication via optical indication device 400. This type of embodiment may be advantageous if cradle 20 is comparatively high-priced and/or has a comparatively long useful life time, resulting in providing additional components as part of cradle 20 being justified. It may further be advantageous if medical device 10 is intended for use in alternative way, e. g. to be carried either without or with cradle, or alternatively with cradle 20 and a simpler low-cost cradle without optical indication device. Here, the embodiment of FIG. 2b is advantageous in so far as indication device control unit 410 is present only in scenarios where actually required.

Figure 2C:
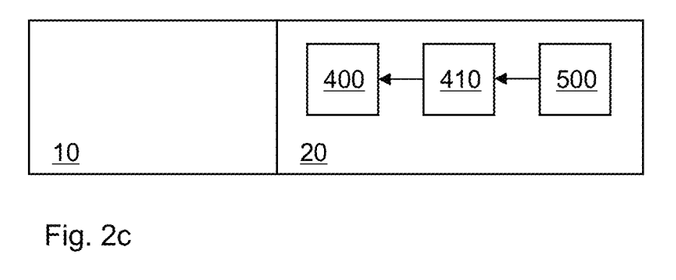

In the embodiment of FIG. 2c, cradle 20 includes continuous glucose monitor 500 with a skin-piercing continuous glucose sensor (not referenced). Optical indication device 400 operatively couples to continuous glucose monitor 500 via indication device control unit 410 to provide glucose information. For the embodiment of FIG. 2c, no operative coupling is present between medical device 10 and optical indication device 400. Cradle 20 is therefore fully operative and may provide glucose indication independent of the presence of medical device 10.

Figure 2D:
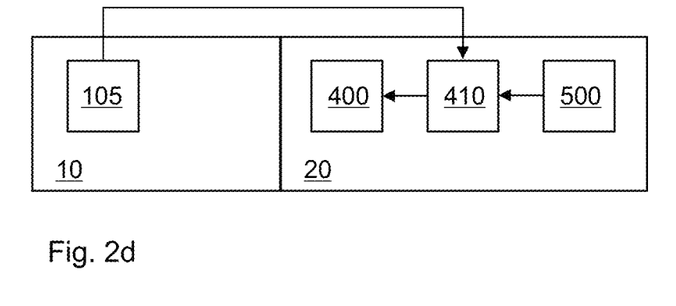

The embodiment of FIG. 2d is similar to the embodiment of FIG. 2c. In addition, however, an operative galvanic or non-galvanic coupling from medical device control circuitry 105 to optical indication device 400 is present via indication device control unit 410. This allows optical indication device 400 to additionally provide indication to the patient with respect to at least one of an operative state or operative parameter of the medical device or the occurrence of a medical device hazard, if medical device 10 is attached to cradle 20. If medical device 10 is temporarily not present, glucose indication can still be provided.

Figure 2E:
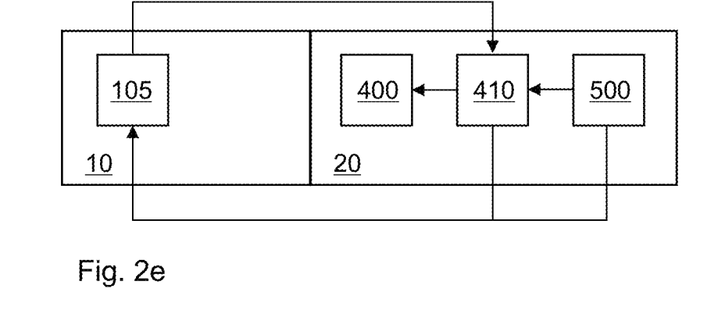

The embodiment of FIG. 2e is similar to the embodiment of FIG. 2d. In addition, however, operative coupling from indication device control unit 410 and/or glucose monitor 500 to medical device control circuitry 105 is present, i.e., coupling between medical device control circuitry and indication device control circuitry 410/glucose monitor 500 is bidirectional. In this way, indications related to operation of the continuous glucose monitor, such as glucose indications, status information or glucose monitor hazards can be transmitted to medical device control circuitry, e.g. for additional indication, storing and record keep, and/or further processing purposes. Information that is received from indication device control circuitry 410 and/or continuous glucose monitor 500 may be simply transmitted or relayed to remote device 600. Alternatively, information may be processed by medical device control circuitry 105.

Figure 2F:
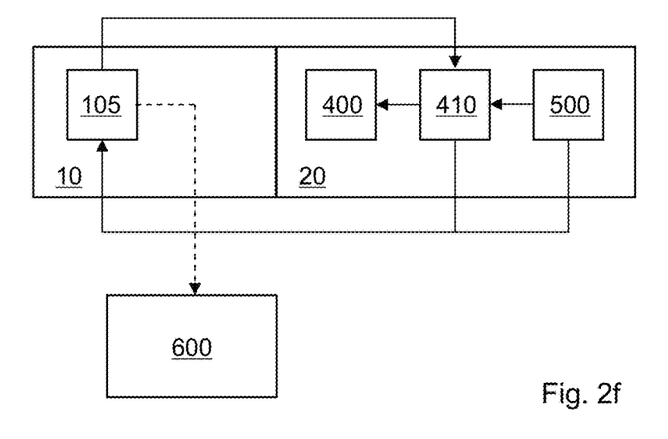

The embodiment of FIG. 2f is similar to the embodiment of FIG. 2e. In addition, however, a remote device 600 is provided and operative coupling, e.g. by wireless RF coupling, is present between medical device control circuitry 105 and remote device 600. Remote device 600 may be a dedicated device of the ambulatory medical system, e.g. in form of a special-purpose remote control device, or may be a general-purpose device, such as a smart phone. Via the operative coupling to remote device 600, glucose indication and/or other useful information that is related to operation of medical device 10 and/or continuous glucose monitor 500 may be transmitted to remote device 600. Remote device 600 may, e.g., include a comparatively large graphical display (not separately shown) which allows comfortable and clear presentation of glucose data in form of tables, graphs, or the like. While not shown, operative coupling between medical device control circuitry 105 and remote device 600 may be bidirectional, thus allowing remote device 600 to provide commands like control instructions to medical device 10 and/or glucose monitor 500.

Figure 2G:
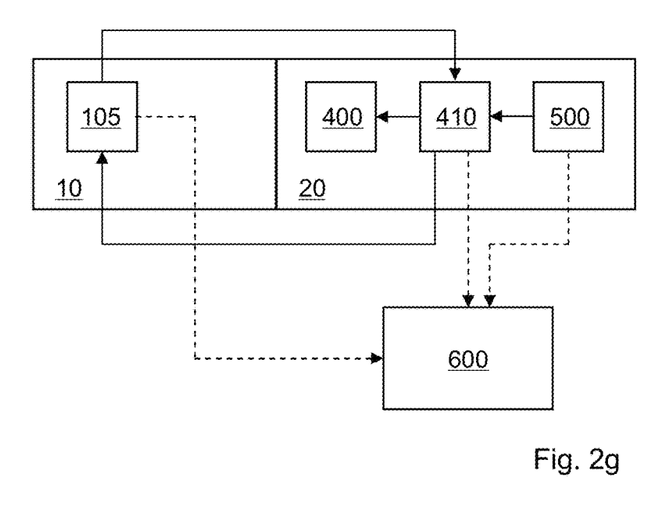

The embodiment of FIG. 2g is similar to the embodiment of FIG. 2f. In addition, however, additional operative coupling is present between indication device control unit 410 and/or glucose monitor 500 to remote device 600. Providing such operative coupling may be advantageous for different reasons. By transmitting data directly to remote device 600, the communication effort between medical device 10 and cradle 20 may be reduced. Additionally or alternatively, data may be transmitted to and indication may be provided by remote device 600 also in situations where medical device 10 is temporarily not present or communication between cradle 20 and medical device 10 and/or communication between medical device 10 and remote device 600 is not established, is disturbed, or the like.

Figure 2H:
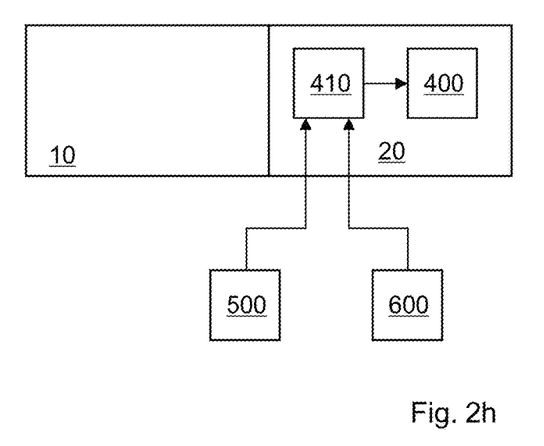

In a further exemplary configuration as shown in FIG. 2h, glucose monitor 500 is a fully separate device that is not realized integral with cradle 20. The indication device of cradle 20, however, is used for providing glucose information to the user as described before. For this purpose, typically wireless operative coupling is present between glucose monitor 500 and indication device control unit 410. Additionally or alternatively, the indication device of cradle 20 may be used for providing optical indications with respect to data originating from remote device 600 in generally the same way. If remote device 600 is, e.g., a remote control device for an insulin infusion pump as exemplary medical device 10, remote device 600 may include a single-spot electrochemical blood glucose meaning device and the indication device of cradle 20 may be used to provide easy accessible and discrete blood glucose readings. While not explicitly shown, operative coupling between medical device 10 and indication device control unit 410 may optionally be additionally present in the same way as described before.

In all of FIG. 2a to FIG. 2g, communication channels are generally shown as being unidirectional, with the direction of information flow being indicated by arrows. It is to be understood however, that alternative bidirectional communication is well possible, thus providing further options and capabilities. In FIG. 2f and FIG. 2g, for example, a communication channel may be present that is directed from remote device 600 to medical device control circuitry 105 and/or indication device control unit 410, thus allowing, e.g., medical device 10 or the optical indication device of cradle 20 to provide indications with respect to data that is generated by or related to operation of remote device 600. Similarly, additional communication channels and operative couplings may be present between devices or units that are not reflected in the figures for clarity reasons. In the configuration of FIG. 2h, for example, direct operative coupling may, e.g. be additionally be present, between remote device 600 and glucose monitor 500, thus allowing remote device 600 to be used as remote control device for glucose monitor 500.

It is further noted that FIG. 2a to FIG. 2g show typical exemplary configurations that may well be combined or modified. Remote device 600, may, e.g. be additionally present in either of the exemplary configurations as shown in FIG. 2a to FIG. 2e.

Figure 3A:
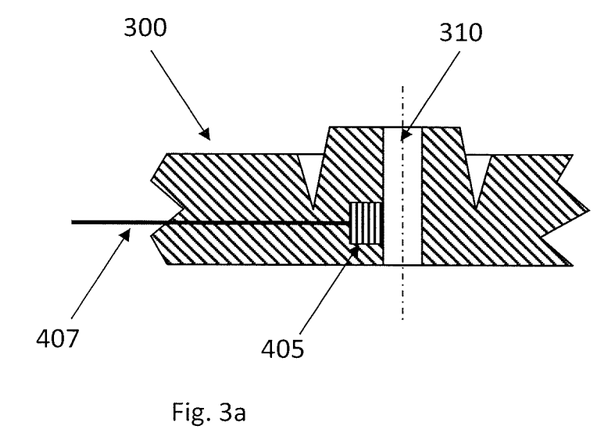
FIGS. 3a and 3b shows the coupling of a cradle and an infusion cannula and a glucose sensor in a schematic way.
Figure 3B:
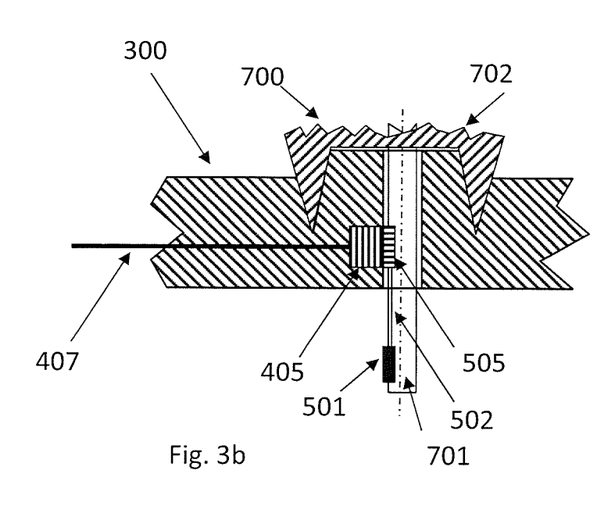

FIG. 3a, 3b exemplary and schematically illustrate the coupling of a cradle in accordance with the present disclosure, e.g. a cradle 20 with cradle base 300 as shown in FIG. 1a, 1b, with an infusion cannula having an integral glucose sensor.

FIG. 3a shows an area of cradle base 300 with well 310 in an enlarged view without an infusion cannula being attached. Cradle base 300 includes one or more electrical cradle connectors(s) 405 that are arranged on an inner surface of—typically but not necessarily—cylindrical well 410. One or more electric cradle line(s) 407 are provided as part of cradle base 300 to provide direct coupling of cradle connector(s) 405 and further components of cradle base 300, such as communication interface, indication device control unit, and LEDs 401a, 401b, 401c. Electric cradle line(s) 407 are exemplarily shown as buried wire(s) that may be realized, e.g., via insert moulding during manufacture of cradle base 300. Alternative technologies, such as screen-printing or MID as mentioned above, may also be used.

FIG. 3b shows an exemplary configuration after attachment of an infusion cannula 700, infusion cannula 700 having a skin-piercing element 701 with a drug-delivery-lumen (not referenced). Infusion cannula 700 may be of substantially rigid material, e.g. medical-grade stainless steel, or may be made of comparatively soft and flexible material, such as Teflon. A piercable septum (not shown) may be present that seals the drug delivery lumen when no infusion device is attached and is pierced by a drug delivery conduit (not shown) of a drug infusion device upon attachment of the drug infusion device to cradle 20. Exemplary infusion cannula 700 further includes hub 702 that is arranged around skin-piercing element 701 and serves for establishing the mechanical connection with cradle base 300 and for aligning skin-piercing element 701 with well 310. The attachment of cradle and infusion cannula 700 may be releasable or non-releasable, e.g. via force-fit or a snap-fit or bayonet connector with a variety of designs being known in the art. In the shown example, a snap-fit or a bayonet connector (not shown) may be present.

Infusion cannula 700 further includes an electrochemical glucose sensor with one or more tissue-contacting sensor electrode(s) 501 which are shown as being arranged on the outer circumferential surface of skin-piercing element 701. Tissue-contacting sensor electrode(s) 501 are placed such that they reside in the subcutaneous tissue after placing the infusion cannula. The infusion cannula further includes cannula connector(s) 505 for establishing a galvanic electric connection of sensor electrode(s) 501, with cannula connector(s) 505 being in galvanic connection with sensor electrode(s) 501 via cannula line(s) 502. In an assembled state, cradle connector(s) 405 and cannula connector(s) are aligned with each other and establish a galvanic connection.

In a variant, skin-piercing element 701 is not part of an infusion cannula but part of a continuous glucose sensor only. In such an embodiment, skin piercing element 701 may not have a lumen. In further variants, skin piercing element 701 may formed integral with or rigidly attached to cradle base 300. In such embodiments, cradle connector(s) 405 and cannula connector(s) 505 may not be present but electric cradle line(s) may be directly coupled to or integral with cannula line(s) 502.

While various embodiments of cradles and methods for their use have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

| Reference signs | |
|---|---|
| 5 | skin |
| 10 | medical device |
| 20 | cradle |
| 105 | medical device control circuitry |
| 110 | indication device control unit |
| 300 | cradle base |
| 302, 304 | anchoring latches |
| 310 | well |
| 400 | optical indication device |
| 401a, 401b, 401c | LEDs |
| 402a, 402b, 402c, 402d | contact elements |
| 405 | cradle connector(s) |
| 407 | cradle line(s) |
| 410 | indication device control unit |
| 500 | continuous glucose monitor |
| 501 | sensor electrode(s) |
| 502 | cannula line(s) |
| 505 | cannula connector(s) |
| 600 | remote device |
| 700 | infusion cannula |
| 701 | skin-piercing element |
| 702 | hub |

The invention claimed is:

1. An ambulatory medical system, comprising:
a cradle having a proximal side and a distal side, the proximal side having a skin attachment member for releasable attachment to a patient's skin, the distal side having a device attachment member configured to attach an initially separate medical device, the cradle comprising:
an electronically controlled optical indication device, the electronically controlled optical indication device being configured to provide a number of distinct color indications each representing a different operative parameter of the medical device to the patient upon attachment of the cradle to the patient's skin and the medical device to the medical device attachment member to establish a galvanic electrical connection of a tissue-contacting sensor electrode with a cradle connector that is electrically connected to the optical indication device, wherein the cradle is formed, at least in part, from an electrochromatic material and/or is coated, at least in part, with an electrochromatic coating, and wherein the electrochromatic material and/or electrochromatic coating serves as the electronically controlled optical indication device, and
the medical device, wherein the medical device comprises medical device control circuitry and an electronic indication device control unit operatively coupled to the medical device control circuitry, wherein the electronic indication device control unit is configured to be operatively coupled to the electronically controlled optical indication device via attachment of the medical device to the cradle to control the electronically controlled optical indication device.

2. The ambulatory medical system of claim 1, further comprising a communication interface operatively coupled to the electronically controlled optical indication device, the communication interface configured to be operatively coupled to the medical device.

3. The ambulatory medical system of claim 1, wherein the electronically controlled optical indication device is configured to provide the distinct color indications in at least two different colors.

4. The ambulatory medical system of claim 1, further comprising an initially separate skin-piercing device which is configured to be attached to the cradle.

5. The ambulatory medical system of claim 4, wherein the skin-piercing device includes an infusion cannula.

6. The ambulatory medical system of claim 4, wherein the skin-piercing device includes an infusion cannula comprising the tissue-contacting sensor electrode and a sensor connector connected to the tissue-contacting sensor electrode, wherein the cradle connector is configured to electrically connect to the sensor connector via the skin-piercing device being attached to the cradle by the skin-piercing device attachment member.

7. The ambulatory medical system of claim 1, wherein the cradle is configured to transmit data provided by a continuous glucose sensor, in an operative state, to the medical device, and/or to a remote device.

8. The ambulatory medical system of claim 7, wherein the cradle is configured to transmit the data provided by the continuous glucose sensor, in an operative state, to the remote device, wherein the remote device is at least one of a remote controller and a smart phone.

9. The ambulatory medical system of claim 1, wherein the electronically controlled optical indication device provides an indication to the patient with respect to both the operative parameter of the medical device and an occurrence of a medical device hazard.

10. The ambulatory medical system of claim 9, wherein the medical device hazard is at least one of an empty drug reservoir, an empty power supply battery, a blocked or leaking infusion line, and an error of the medical device.

11. The ambulatory medical system of claim 1, wherein the medical device includes a drug infusion device, the drug infusion device including an infusion cannula or an outlet that is designed to fluidically couple to an infusion cannula comprised by or attached to the cradle.

12. The ambulatory medical system of claim 1, wherein the medical device includes continuous glucose monitor circuitry.

13. The ambulatory medical system of claim 1, wherein the optical indication device provides optical indications which are one or more of: an indication of a reservoir being filled to a predetermined fraction of its full volume, an indication of attachment of the cradle to the patient's skin, an indication of occurrence of a medical device hazard, an indication with respect to data that originates from a remote device that is generated by or related to operation of the remote device, and an indication of an alert to the patient of an action or system check to be carried out by the patient.

14. A method for providing optical indications to a patient carrying an ambulatory medical system, comprising:
providing a cradle and a medical device, the cradle having a proximal side and a distal side, the proximal side having a skin attachment member for releasable attachment to a patients skin, the distal side having a device attachment member for attaching the medical device, the medical device being initially separate, the cradle comprising:
an electronically controlled optical indication device, the electronically controlled optical indication device being configured to provide a number of distinct color indications each representing a different operative parameter of the medical device to the patient upon attachment of the cradle to the patient's skin and the medical device to the medical device attachment member to establish a galvanic electrical connection of a tissue-contacting sensor electrode with a cradle connector that is electrically connected to the optical indication device, wherein the cradle is formed, at least in part, from an electrochromatic material and/or is coated, at least in part, with an electrochromatic coating, and wherein the electrochromatic material and/or electrochromatic coating serves as the electronically controlled optical indication device, wherein the medical device comprises medical device control circuitry and an electronic indication device control unit operatively coupled to the medical device control circuitry, wherein the electronic indication device control unit is configured to be operatively coupled to the electronically controlled optical indication device via attachment of the medical device to the cradle;
attaching the medical device to the cradle; and
controlling, by the electronic indication device control unit, the electronically controlled optical indication device to provide the optical indications.

15. The method of claim 14, wherein the medical device includes a drug infusion device, the drug infusion device being configured to subcutaneously deliver a drug, and said method further comprises:
controlling the optical indication device to provide an indication to the patient with respect to both the operative parameter and the occurrence of a drug infusion hazard.

* * * * *